United States Patent [19]

Okumura et al.

[11] 4,456,592

[45] Jun. 26, 1984

[54] ANTIBIOTICS, NEOVIRIDOGRISEINS, AND THEIR METHOD OF PRODUCTION

[75] Inventors: Yasushi Okumura; Kazuhiko Okamura; Yasuo Fugakawa; Tomoyuki Ishikura, all of Kanagawa; Kageaki Kouno, Tokyo, all of Japan; Joseph Lein, Fayetteville, N.Y.

[73] Assignees: Sanraku-Ocean Co.; Panlabs Inc., both of Tokyo, Japan

[21] Appl. No.: 333,950

[22] Filed: Dec. 23, 1981

Related U.S. Application Data

[62] Division of Ser. No. 803,922, Jun. 6, 1977, Pat. No. 4,355,112.

[51] Int. Cl.³ .................. A61K 37/00; C07C 103/52
[52] U.S. Cl. .................. 424/177; 260/112.5 R
[58] Field of Search .................. 260/112.5 R; 424/177

[56] References Cited

U.S. PATENT DOCUMENTS

| | | | |
|---|---|---|---|
| 3,137,640 | 6/1964 | Watanabe et al. | 260/112.5 R |
| 3,299,047 | 1/1967 | Bodanszky et al. | 260/112.5 R |
| 3,373,151 | 3/1968 | Bodanszky et al. | 260/112.5 R |
| 3,420,816 | 1/1969 | Bodanszky | 260/112.5 R |
| 3,719,656 | 3/1973 | Jolles | 260/112.5 R |

*Primary Examiner*—Delbert R. Phillips

[57] ABSTRACT

A group of novel depsipeptide antibiotics, neoviridogriseins I, II and III are produced by fermentation of Streptomyces sp. P8648 (FERM-P 3562; ATCC 31289). The antibiotics are highly active against Gram-positive bacteria and mycoplasmas.

14 Claims, 12 Drawing Figures

INFRARED SPECTRUM OF NEOVIRIDOGRISEIN II (KBr TABLET)

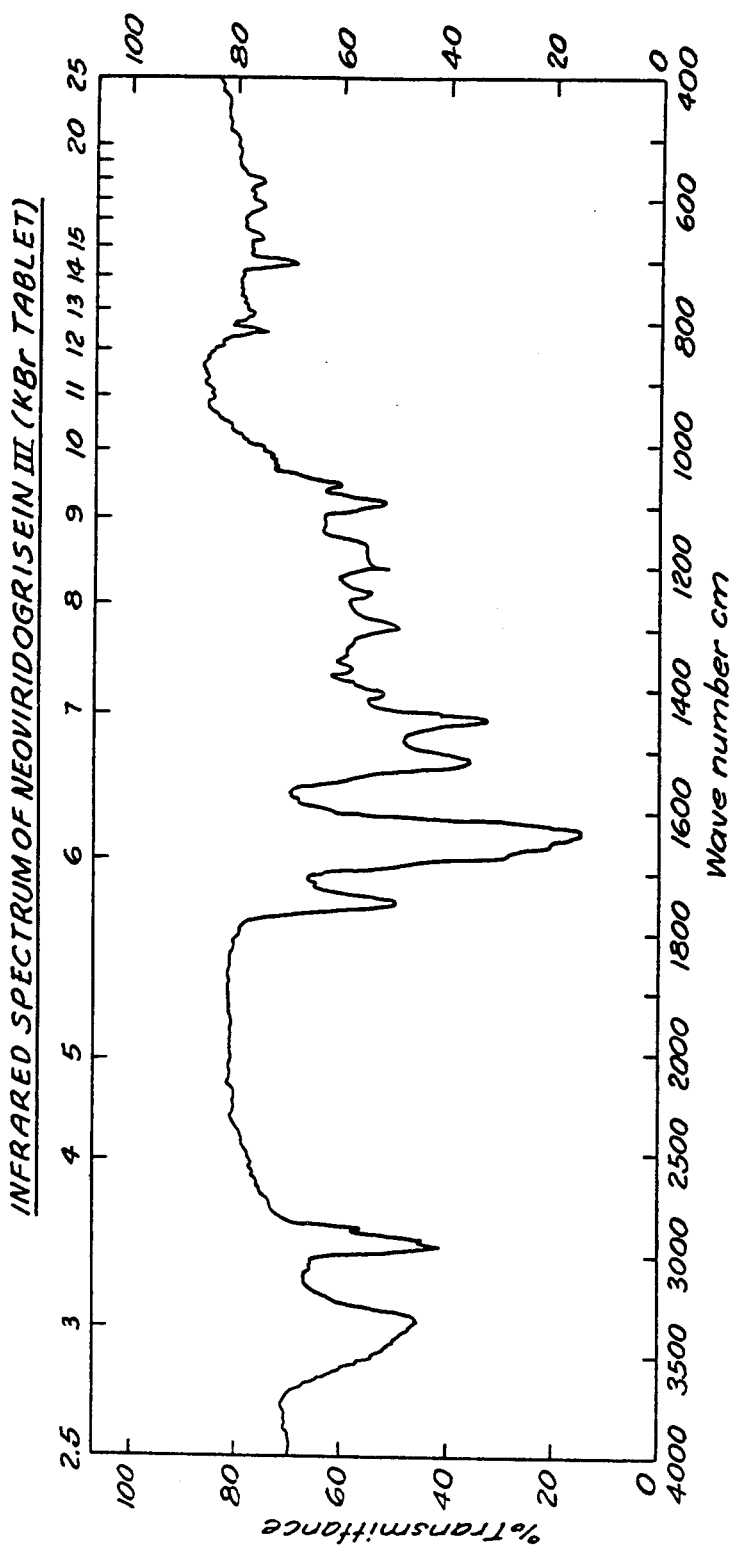

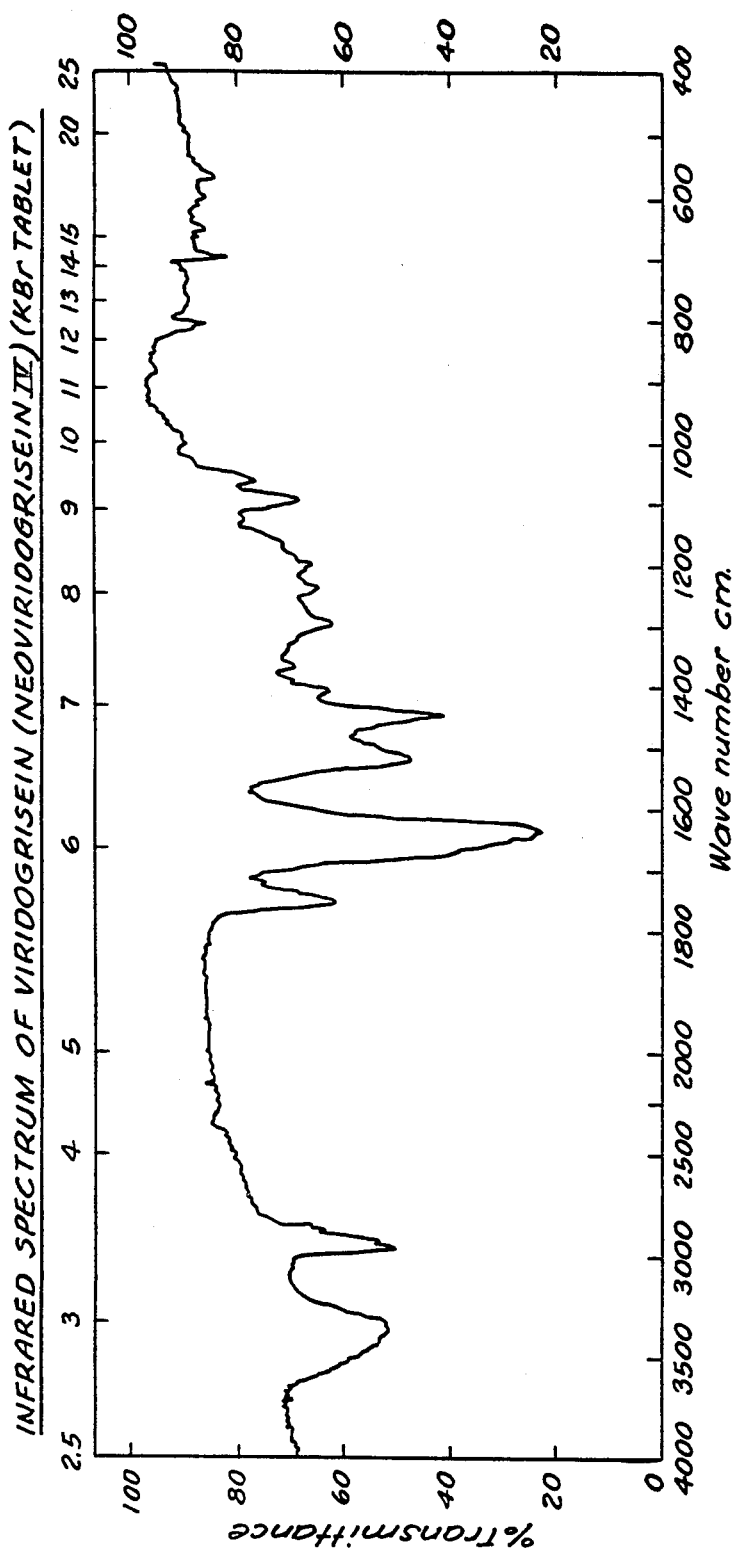
Fig. 12 INFRARED SPECTRUM OF VIRIDOGRISEIN (NEOVIRIDOGRISEIN Ⅳ) (KBr TABLET)

ANTIBIOTICS, NEOVIRIDOGRISEINS, AND THEIR METHOD OF PRODUCTION

This is a divisional of application Ser. No. 803,922, filed June 6, 1977, now U.S. Pat. No. 4,355,112.

BACKGROUND OF THE INVENTION (1) Field of the Invention

This invention relates to new depsipeptide antibiotics, called neoviridogriseins I, II and III; to their production and isolation; and to their utilization as therapeutic drugs and animal feed additive.

(2) Description of the Prior Art

The mikamycin-vernamycin (or streptogramin) family of antibiotics are classified into two major groups. One major group (Group A according to D. Vazquez; pp521–534, ANTIBIOTICS III, Mechanism of action of antimicrobial and antitumor agents, Springer-Verlag Berlin Heidelberg New York 1975) is a macrocyclic lactone compound, and includes griseoviridin, ostreogrycin A(=mikamycin A=virginiamycin M=staphylomycin M=pristinamycin IIA=vernamycin A=streptogramin A=synergistin A-1=Compound PA-114A1=Compound E-129 Factor A, etc.), ostreogrycin G (=virginiamycin MII=staphylomycin MII=pristinamycin IIB=dihydrostreogrycin A=Compound E-129 Factor B=Compound R.P.-13920, etc.), and Compounds A-2315 A, B and C. Though bacteriostatic, this group of antibiotics are active against Gram-positive bacteria and mycoplasmas. Griseoviridin, which is one of the fermentation products in this invention, is known to be produced together with viridogrisein by streptomycetes, and the production of griseoviridin is disclosed in U.S. Pat. Nos. 3,023,204 and 3,174,902. The other major group (Group B according to D. Vazquez) is a macrocyclic depsipeptide compound and divided into two sub-groups, that is, the viridogrisein sub-group and the vernamycin B sub-group. The antibiotics in this major group are mainly effective in suppressing the growth of Gram-positive bacteria such as *Staphylococcus aureus* and *Bacillus subtilis*. The vernamycin B sub-group contains 12 homologues. Because the synonym relationships among the published names of antibiotics in this group are so complicated, it is practically impossible to list all the compound names of this sub-group. Some representative, and scientifically important, compounds of this sub-group are as follows:

1. Vernamycin B=ostreogrycin B=pristinamycin IA=mikamycin B=streptogramin B=synergistin B-1=compound E-129 Factor Z=compound PA114B1.
2. Vernamycin B=ostreogrycin B1=pristinamycin IC=compound E-129 Factor Z1.
3. Vernamycin B=ostreogrycin B2=pristinamycin IB=compound E-129 Factor Z2=compound R.P.-13919.
4. Ostreogrycin B3=compound E-129 Factor Z3.
5. Patricin A
6. Patricin B
7. Vernamycin B$_\delta$
8. Vernamycin C=doricin
9. Virginiamycin (Staphylomycin)S
10. Virginiamycin(Staphylomycin)S2
11. Virginiamycin (Staphylomycin)S3
12. Virginiamycin (Staphylomycin)S4 (or S1)

The compounds of this sub-group have the common feature that they are composed of seven constituents sharing in the same four constituents of 3-hydroxypicolinic acid, L-threonine, L-proline and L-phenylglycine. On the other hand, in the viridogrisein sub-group there has been known only one compound, viridogrisein, and the identity with viridogrisein of etamycin, compound K-179 and compound F-1307A is well established. In contrast to the above vernamycin B sub-group, viridogrisein is composed of 8 constituents, that is, 3-hydroxypicolinic acid, L-threonine, D-leucine, 4-hydroxy-D-proline, sarcosine, β,N-dimethyl-L-leucine, L-alanine and L-phenylsarcosine. As apparent in the following detailed description of the invention, the neoviridogrisein antibiotics of this invention belong to this viridogrisein sub-group, and one of the compounds, neoviridogrisein IV, has been identified as viridogrisein. Preparation of viridogrisein is disclosed in U.S. Pat. No. 3,023,204.

The synergism between Group A and Group B is well known on various microorganisms, and profitably utilized to potentiate the therapeutic efficiency of pharmaceutical drugs containing the antibiotic of this family as active components. This is true of neoviridogriseins, too.

SUMMARY OF THE INVENTION

This invention relates to novel and useful depsipeptide antibiotic substances. More particularly, it relates to a group of depsipeptide antibiotics called neoviridogriseins I, II and III and viridogrisein. They are active against Gram-positive bacteria and mycoplasmas, and can be used in diluted forms, as crude concentrates, or in pure form, together with or without griseoviridin.

It is an object of the present invention to provide a group of new depsipeptide antibiotics called neoviridogriseins, I, II and III which are highly effective in inhibiting the growth of various Gram-positive bacteria and mycoplasmas.

Another object of this invention is to give a method for the preparation of these depsipeptide antibiotics by fermenting a suitable aqueous medium under aerobic conditions by a new species of Streptomyces named Streptomyces sp. P8648 (FERM-P3562; ATCC31289) whereby formed neoviridogriseins are recovered from the fermentation broth together with or without griseoviridin.

It also is another object of the present invention to provide a method for the selective production of the desired neoviridogrisein component(s) by supplementing some pertinent amino acid(s), more particularly, proline to increase neoviridogriseins I and II, and alpha-amino-n-butyric acid to increase neoviridogriseins I and III, during or before fermentation. Other objects will be apparent from the detailed description of the invention. Neoviridogriseins I, II and III of the present invention are valuable antibiotics which are highly active against various pathogenic microorganisms including Gram-positive bacteria and mycoplasma, and, accordingly, find utility in human and veterinary medicine. More practically, the antibiotics of this invention can be used as therapeutic drugs for the treatment of infections diseases caused by Gram-positive bacteria and mycoplasma, for example, *Staphylococcus aureus, Streptococcus pyogenes, Diplococcus pneumoniae, Mycoplasma gallisepticum, Mycoplasma fermentans, Mycoplasma agalactiae*, etc.

In this invention, the unmodified term "neoviridogrisein" is used to generically designate depsipeptide antibiotics called neoviridogriseins; that is, it means not only a member in the group of neoviridogriseins I, II and III and viridogrisein(=neoviridogrisein IV), but also a mixture of any two or more members selected from the said group.

DETAILED DESCRIPTION OF THE INVENTION

Microorganism

The new depsipeptide antibiotics of the invention are produced by a new strain of Streptomyces called Streptomyces sp.P8648 (FERM-P 3562; ATCC 31289) together with viridogrisein and griseoviridin. This microorganism has been isolated from a soil sample collected near the Kuzuryu dam in Fukui-ken.

Generally, the microorganism of this invention elongates colorless, short aerial mycelia from well-branched (single branching) substrate mycelia. Spore chains with smooth surface are formed in a loose loop on top of aerial mycelia. Neither whirl nor ascospore is observed. The cultural characteristics of this microorganism on various agar media are described as follows:

(1) Sucrose-nitrate agar
  Growth: Poor.
  Aerial mycelium: Thin, white aerial mycelia occasionally formed.
  Reverse: Colorless to grayish white.
  Soluble pigment: None.

(2) Glucose-asparagine agar
  Growth: Abundant.
  Aerial mycelium: Little or none. When formed, white.
  Reverse: Pale yellowish white to light yellow.
  Soluble pigment: None.

(3) Glycerin-asparagine agar
  Growth: Moderate.
  Aerial mycelium: Little or none. When formed, white.
  Reverse: Pale yellow to grayish yellow.
  Soluble pigment: None.

(4) Yeast extract-malt extract agar
  Growth: Abundant.
  Aerial mycelium: White to white with grayish tinge.
  Reverse: Light yellow, later turning to brownish gray.
  Soluble pigment: None or rarely slight brown.

(5) Starch agar
  Growth: Moderate.
  Aerial mycelium: None or little. When formed, white.
  Reverse: Pale yellow with light grayish tan in the center of colonies.
  Soluble pigment: None.
  Starch hydrolysis: Poor.

(6) Tyrosine agar
  Growth: Moderate.
  Aerial mycelium: None or a few spots of white aerial myceliul occasionally observed.
  Reverse: Grayish yellow to light yellowish tan.
  Soluble pigment: Initially pale purple to light reddish brown, 10 days later turning to pale brown. Little melanoid pigment formed.

(7) Nutrient agar
  Growth: Good.
  Aerial mycelium: Thin, white.
  Reverse: Pale yellow.
  Soluble pigment: None.

(8) Oatmeal agar
  Growth: Good.
  Aerial mycelium: White to grayish white.
  Reverse: Grayish yellow to light reddish brown with grayish tinge.
  Soluble pigment: None.

The optimum growth temperature for the microorganism of this invention is in the range of 25°–35° C. Though the growth is very poor, the microbe can grow even at a temperature beyond the said temperature range like 10° C. or 45° C. But it can not grow at a temperature of 52° C.

This actinomycete liquefies gelatin in glucose-peptone-gelatin medium; weakly hydrolyzes starch in starch-inorganic salts agar; and peptonizes skimmed milk without coagulation.

Production of melanoid pigment is occasionally observed in tyrosine agar, but not in peptone-yeast extract-iron agar and tyrosine-yeast extract broth.

Carbon source assimilation pattern of this microorganism is as follows (in Pridham-Gottlieb's medium):
Positive: D-Xylose, D-glucose, D-fructose L-rhamnose, D-mannitol.
Slightly positive: Sucrose.
Negative: L-Arabinose, i-inositol, raffinose.

In relation to the production of the known peptide and non-peptide macrolide antibiotics like mikamycins A and B, virginiamycins, ostreogrycins, etamycin, vernamycins, viridogrisein, griseoviridin and pristinamycins, the following microorganisms should be compared with Streptomyces sp. P8648:

Streptomyces griseus NRRL 2426
  griseoviridus NRRL 2427
  sp., etamycin producer
  conganensis
  ostreogriseus
  mitakaensis
  loidensis The available information on the cultural and physiological characteristics of the said microorganisms shows clear differences between the streptomycete claimed in this invention and the above-mentioned ones. For example, Streptomyces griseus NRRL 2426 differs in that it belongs to the Section Rectiflexibiles with straight or slightly wavy spore chains while the microorganism of this invention is included in the Section Spirales; that the former produces gray to yellowish gray aerial mycelia on yeast extract-malt extract agar while the latter produces white to grayish white aerial mycelia; and that the former utilizes L-arabinose while the latter does not. Streptomyces sp., etamycin producer which has been specified in Antibiotics Annual 1954–1955, pp. 728–732, can be differentiated from the microorganism of this invention in the assimilation pattern of carbon sources and the cultural characteristics on Czapek agar, glucose-asparagine agar and nutrient agar. Streptomyces conganensis shows clear differences in the morphological characteristics of spores. Among the above-listed microorganisms, Streptomyces griseoviridus NRRL 2427 looks most similar to the streptomycetes of this invention. The results of the taxonomical comparison between the said two type cultures are summarized in the following table:

| | *Streptomyces griseoviridus* NRRL 2427 | | *Streptomyces* sp. P 8648 | |
| --- | --- | --- | --- | --- |
| Color of aerial mycelium | Pale orangish yellow to yellowish pink with gray tinge on yeast extract-malt extract agar, oatmeal glycerin-asparagine agar. | | White to grayish white aerial mycelium poorly formed on most ISP media. White aerial mycelium abundantly formed on extract agar. | |
| Color or substrate mycelium 2 | Grayish yellow to olivish brown or blackish brown on yeast extract-malt extract agar, oatmeal agar, starch agar and glycerin-asparagine agar. | | Pale yellow or light yellow to grayish brown on most ISP media. | |
| Soluble pigment | No melanoid pigment formed. No other pigment usually observed, but rarely yellow pigment poorly formed. | | No melanoid pigment formed. No other pigment usually observed, but rarely brown pigment slightly formed. | |
| Utilization of carbon sources | L-arabinone<br>D-fructose<br>sucrose | +++<br>±<br>− | L-arabinose<br>D-fructose<br>sucrose | −<br>+++<br>± |

As apparent from the preceeding table, clear differences have been confirmed between *Streptomyces griseoviridus* NRRL 2427 and the streptomycete of this invention in the morphological and cultural characteristics and the utilization pattern of carbon sources. In addition, when both are fermented under identical conditions, the microorganism of this invention can produce neoviridogriseins I, II and III as well as viridogrisein(neoviridogrisein IV) and griseoviridin, while the type culture of *Streptomyces griseoviridus* NRRL 2427 produces only viridogrisein and griseoviridin, but not neoviridogriseins I, II and III.

From the above described results, the microorganism employed in this invention has been concluded to be a new species of Streptomyces and named Streptomyces sp. P 8648. The type culture of this microorganism has been deposited with the Fermentation Research Institute, Agency of Industrial Science and Technology, with the deposition number of FERM-P No. 3562. It has also been deposited with the American Type Culture Collection where it was assigned the code number ATCC 31289.

It may be well understood to those skilled in the art that this invention is not limited to the particular microorganism which has been specified above and filed as FERM-P No. 3562 to Fermentation Research Institute, but includes all those spontaneous and artificial mutants derived from the said microorganism which are capable of producing the new antibiotics, neoviridogrisein I, II and III.

PRODUCTION OF NEOVIRIDOGRISEINS I, II, and III

The new antibiotics of this invention are produced by inoculating and propagating Streptomyces sp. P8648 in a suitable medium under aerobic conditions at a temperature in the range of 18°–37° C. for a period of 2–14 days whereby the accumulated antibiotics are recovered from the fermentation broth and purified by conventional methods. The preferred embodiments of the processes according to this invention will be illustrated in more detail in the following:

For the fermentation of the microorganism of this invention, employable are all kinds of media which have been well known as media for Streptomycetes. For example, preferable carbon sources of the medium are glucose, glycerin, starch, dextrin, oatmeal, molasses, fat and oil and the like. Suitable nitrogen sources for the purposes of this invention are: soybean meal, cotton seed meal, meat extract, peptone, dry yeast, corn steep liquor, yeast extract, casein and its hydrolysate and inorganic salts such as ammonium sulfate and ammonium nitrate. If desired, minor growth factors may be added to the medium. They include vitamins, aminoacids, organic and inorganic salts such as calcium carbonate, sodium chloride, potassium chloride, sodium phosphate, potassium phosphate and magnesium sulfate.

The new antibiotics of this invention can be produced by fermentation in traditional vessels such as a shake flask, a jar fermentor and a tank fermentor, but economically, the submerged cultivation under forced aeration will be most advantageous in an industrial scale. The fermentation is desirably carried out under aerobic conditions at a temperature in the range of 25°–35° C. When a shake flask or a tank fermenter is employed, the production of neoviridogriseins reaches a peak usually in 2–10 days. The pH value during fermentation may change beyond the physiological range, depending on the kind of medium employed. It is more desirable to adjust and maintain the pH value during fermentation in the range of 6–9. Usually the pH of the medium is adjusted to 6.5–8.5 before inoculation.

CONTROL OF THE NEOVIRIDOGRISEIN COMPONENTS IN THE FERMENTATION BROTH

As described above, the microorganism of this invention produces a mixture of neoviridogriseins I, II, III and IV and griseoviridin. It is possible to change the composition of neoviridogriseins in the fermentation broth by a suitable combination of carbon and nitrogen sources in the medium without the specific addition of either a free aminoacid or an organic acid. But it will be more profitable from the viewpoint of industrial production to adjust the content of neoviridogriseins I, II and/or III in the fermentation broth by adding to the medium the pertinent constituent amino acid(s) in free form during fermentation, depending on the circumstances and the demand. The composition of neoviridogriseins in the fermentation broth may be varied appropriately by selecting spontaneous or artificial mutants derived from the type culture of the streptomycete of this invention; by adjusting fermentation conditions like temperature, pH and aeration; and/or by adding to the medium physiologically active agents such as enzyme inhibitors and promoters. One of the preferred embodiments of methods for selective production of particular neoviridogrisein components consists of feeding the pertinent constituent amino acid(s), alpha-amino-n-butyric acid and/or proline during fermentation. More particularly, the addition of proline during fermentation increases the percentage of neoviridogriseins I and II in the total amount of neoviridogriseins I, II, III and IV, which are more potent in antimicrobial activities than neoviridogriseins III and IV. This is also true of alpha-amino-n-butyric acid. The amount of neoviridogriseins I and III can be selectively increased by feeding alpha-amino-n-butyric acid to the medium before inoculation or during fermentation. As the microorganism of this invention produces protease during growth, proteinaceus material which contains the said pertinent constituent amino acid(s) may be added instead of the free amino acid(s). For example, proline can be substituted by casein or corresponding hydrolysates from acid hydrolysis such as, for instance, casamino acids.

ISOLATION AND PURIFICATION

The new antibiotics, neoviridogriseins I, II and III and viridogrisein can be isolated from the fermentation broth by conventional methods based on their physico-chemical properties as depsipeptide antibiotics. If necessary, neoviridogriseins may be recovered from the fermentation broth together with griseoviridin as a neoviridogriseins-griseoviridin mixture. When they are prepared for feed additive or veterinary drug use, a crude mixture of neoviridogriseins and griseoviridin will be more advantageous economically.

Neoviridogriseins and griseoviridin in the fermentation broth can be extracted with a water-immiscible organic solvent. For example, ethyl acetate, butyl acetate, n-butanol, methylene chloride, chloroform, and the like are suitable for extraction of neoviridogriseins and griseoviridin at one time. When it is more desirable to selectively extract neoviridogriseins without griseoviridin, preferred organic solvents are methyl isobutyl ketone, benzene, toluene and other aromatic hydrocarbons. As the mycelium substantially contains no neoviridogriseins and the extractable lipid in cells may often interfere with subsequent purification steps, it is more profitable to extract the said antibiotics with an organic solvent from the filtered broth or centrifuged broth together with the water wash.

The solvent extract of neoviridogriseins and/or griseoviridin can be further isolated and purified in a number of different ways. For example, adsorption and elution processes with active carbon, Amberlite XAD-4 and 7 (Rohm & Haas Co.), ion exchange resins such as Amberlite IR-120 (Rohm and Haas Co.) and Dowex 50W-X2 (The Dow Chemical Co.); gel filtration with Sephadex LH-20 (Pharmacia Fine Chemicals AB) and its equivalents; adsorption chromatography on alumina and silica gel, etc. can be conveniently combined for isolation and purification. In addition, countercurrent distribution with a suitable solvent system may work well for the said purposes.

PHYSICO-CHEMICAL PROPERTIES OF NEOVIRIDOGRISEINS I, II and III

Neoviridogriseins I, II and III as well as viridogrisein are amorphous white solids and are soluble in methanol, ethanol, n-propanol, iso-propanol, n-butanol, dioxane, ethyl acetate, butyl acetate, acetone, methyl ethyl ketone, methyl isobutyl ketone, benzene, toluene, methylene chloride, chloroform, carbon tetrachloride, N,N-dimethylformamide and dimethyl sulfoxide; hardly soluble in water and ethyl ether; and practically insoluble in petroleum ether and hexane.

They are stable in aqueous solution for at least one month at a temperature in the range of 25°-37° C.; and for 30 minutes at 60° C., at a pH of 2-9. The melting points of the antibiotics were determined in a Kofler apparatus and the following results were obtained:

| Neoviridogrisein | I | not determined |
| | II | 93° C. |
| | III | 115° C. |

| -continued | |
|---|---|
| Viridogrisein | 40° C. |

The ultraviolet absorption spectra of neoviridogriseins I, II, III and viridogriseins are reproduced in FIGS. 1-8 wherein FIGS. 1-4 show the U.V. spectrum of neoviridogrisein I, II, III and viridogrisein when registered in methanol and FIGS. 5-8 the U.V. spectrum of the same substances registered in 0.1N NaOH-methanol. The $E_{1\ cm.}^{1\%}$ value of neoviridogrisein at their maxima is as follows:

In neutral methanol,

| Neoviridogrisein | I | 205 nm(65) |
| | II | 205 nm(88) |
| | III | 205 nm(90) |
| Viridogrisein | | 205 nm(90) |

In 0.1N NaOH-methanol,

| Neoviridogrisein | I | 240 nm(70) |
| | II | 240 nm(84) |
| | III | 240 nm(96) |
| Viridogrisein | | 240 nm(96) |

The infrared absorption spectra of neoviridogriseins I, II, III and viridogrisein, in a KBr tablet are shown in FIGS. 9-12 respectively. The characteristic peaks and shoulders are observed at the following wave numbers:

Neoviridogrisein I (KBr tablet): 3370, 2910, 2850, 1735, 1670(sh.), 1635,1590(sh.), 1515,1460(sh.) 1445,1405,1375,1290,1280,1250(sh.),1200,1190,1160,11-25,1100, and 1080 cm.$^{-1}$ Neoviridogrisein II(KBr tablet): 3320, 2950,2920,2820,2800,1745,1670(sh.),1630,1600(sh.),157-5, 1515,1460(sh.) 1445,1405,1390,1365,1330(sh.),1295,1275,1240,1200, 1195,1160,1130,1095 and 1065 cm.$^{-1}$ Neoviridogrisein III(KBr tablet): 3335,2960,2940,2870,1750,1670(sh.),1660(sh.),1635,159-0(sh.);1515, 1450,1405,1390(sh.), 1370,1340(sh.),1300,1245,1200,1160(sh.),1130, 1100 and 1065 cm.$^{-1}$ In the thin layer chromatography systems indicated below, neoviridogriseins I, II and III viridogrisein and griseoviridin have the following Rf values:

| (1)TLC plate | | Pre-coated TLC plate SILICA GEL 60F-254, E. Merck, Darmstadt. |
|---|---|---|
| Solvent | | Benzene:methanol = 5:1 |
| Neoviridogrisein | I | Rf = 0.66 |
| | II | 0.62 |
| Neoviridogrisein | III | Rf = 0.59 |
| Viridogrisein | | 0.55 |
| Griseoviridin | | 0.20 |
| (2) TLC plate | | Same as (1) |
| Solvent | | Chloroform:methanol = 30:1 |
| Neoviridogrisein | I | Rf = 0.39 |
| | II | 0.32 |
| | III | 0.19 |
| Viridogrisein | | 0.18 |
| Griseoviridin | | 0.02 |

For the analysis of the constituent amino acids, each neoviridogrisein component was hydrolysed in 6N HCl overnight at 110° C. and the resulting hydrolysate was evaporated to dryness. After even a trace of hydrochloric acid was removed by repeated evaporations, amino acids in the hydrolysate were determined by thin layer chromatography (Eastman Chromagram sheet 13254 cellulose with fluorescent indicator, Eastman Kodak Co.; solvent system: n-butanol/acetic acid/water=4/1/1), high voltage paper electrophoresis (Toyo Filter paper No. 51A, Toyo Roshi Kaisha, Ltd.; buffer system: formic acid/acetic acid/water=25/75/900, pH=1.8; 60 V/cm at 0° C. for 30 minutes) and auto-amino acid analysis (Hitachi auto-amino acid analyser KLA-5, Hitachi, Ltd.). The presence of the following amino acids was confirmed:

| Neoviridogrisein I | threonine |
| | leucine |
| | proline |
| Neoviridogrisein I | alpha-amino-n-butyric acid |
| | sarcosine |
| | phenylsarcosine |
| | β,N—dimethylleucine |
| Neoviridogrisein II | threonine |
| | leucine |
| | proline |
| | alanine |
| | sarcosine |
| | phenylsarcosine |
| | β,N—dimethylleucine |
| Neoviridogrisein III | threonine |
| | leucine |
| | hydroxyproline |
| | alpha-amino-n-butyric acid |
| | sarcosine |
| | phenylsarcosine |
| | β,N—dimethylleucine |
| Viridogrisein | threonine |
| | leucine |
| | hydroxyproline |
| | alanine |
| | sarcosine |
| | phenylsarcosine |
| | β,N—dimethylleucine |

The presence of 3-hydroxy-pycolinic acid was confirmed by mass spectrometry and thin layer chromatography as follows:

An authentic sample of viridogrisein and each of neoviridogriseins I, II, III and IV were hydrolysed overnight in 6N HCl at 110° C. to give the hydrolysates as described above. Each hydrolysate showed only one UV-absorbing spot with the same Rf value under the indicated conditions.

(1) Silica gel TLC
  TLC plate: Pre-coated TLC plate SILICA GEL 60 F-254, E. Merck, Darmstadt.
  Solvent: Chloroform:methanol=2:1
  Rf: 0.46
(2) Cellulose TLC
  TLC plate: Eastman Chromagram sheet 13254 cellulose with fluorescent indicator, Eastman Kodak Co.
  Solvent: n-Butanol:acetic acid:water=4:1:1
  Rf: 0.62

The molecular weight of these antibiotics was determined by direct insertion into a mass spectrometer.

| Neoviridogrisein | I | 876 |
| | II | 862 |
| | III | 892 |
| Viridogrisein | | 878 |

For the study on the chemical structure of neoviridogriseins I, II and III, these three new antibiotics and viridogrisein were hydrolysed overnight in 0.1N NaOH at room temperature and then methylated with diazomethane before mass spectrometry according to the method of Compernolle et al. (Organic Mass Spectrometry, Vol. 6, pp151-166, 1972). The structure of neoviridogriseins I, II and III is concluded from the available information described above to be as follows:

Neoviridogrisein I

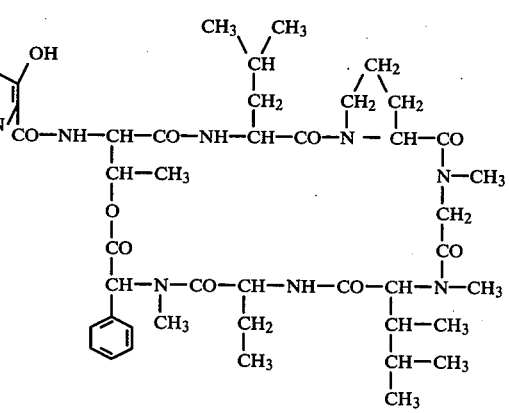

Neoviridogrisein II

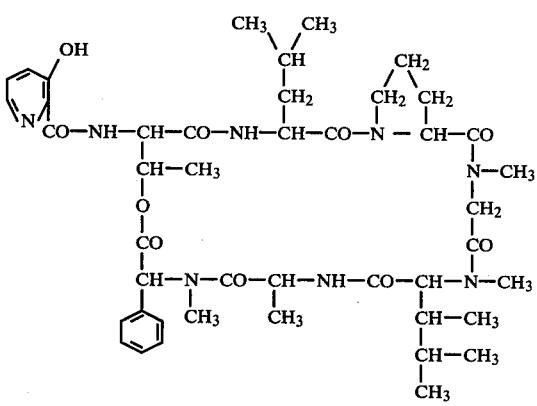

Neoviridogrisein III

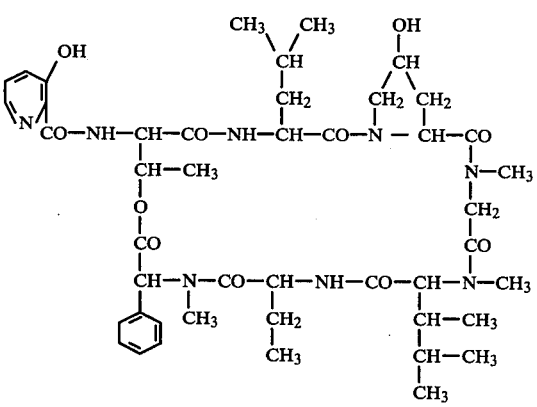

As can be seen from the preceding structures of neoviridogriseins I, II and III, the antibiotics of the invention are a group of new depsipeptide antibiotics homologous to viridogrisein. The identity of neoviridogrisein IV with viridogrisein and etamycin was confirmed by mass spectrometry, thin layer chromatography, UV and IR spectrometry and amino acid analysis, using authentic samples of viridogrisein and etamycin.

ANTIMICROBIAL ACTIVITY

Neoviridogrisein I, II and III have a broad antimicrobial spectrum against bacteria, mycoplasmas, actinomycetes and rickettsiae in laboratory test. More exactly, they display a remarkable activity in vitro against the usual and resistant strains of *Staphylococcus aureus*, as well as strains of *Streptococcus pyogenes*, *Diplococcus pneumoniae*, *Sarcina lutea*, *Bacillus subtilis*, *Mycoplasma gallisepticum*, *Mycoplasma pulmonis*, *Mycoplasma fermentans* and *Mycoplasma agalactiae*. The minimal inhibitory concentrations of the new depsipeptide antibiotics of this invention were determined separately and together with viridogrisein and griseoviridin on various microorganisms by the tube dilution method. The results are shown in the following tables:

TABLE 2-continued

| Comparison of neoviridogrisein II with viridogrisein | | |
|---|---|---|
| | MIC (mcg/ml) | |
| Microorganism | NV*II | VG** |
| Russell(PC)' | 0.125 | 0.267 |
| Smith | 0.125 | 0.267 |

Medium: brain heart infusion broth
Abbreviation: as listed above.

When the minimal inhibitory concentrations of neoviridogriseins I, II and III were tested in the presence of griseoviridin, the synergism was observed between the neoviridogrisein member and griseoviridin, as is the case of viridogrisein and griseoviridin. Therefore the synergistic phenomenon of the new antibiotics of this invention with griseoviridin was studied in more detail with the varied ratios of the neoviridogriseins mixture to griseoviridin. The obtained results are shown in the following table:

TABLE 1

| | MIC values of neoviridogriseins I, II and III (mcg/ml) | | | | | | |
|---|---|---|---|---|---|---|---|
| Microorganism (a) | Medium | NV*I | NV*II | NV*III | VG** | NV*mix. | NV* - GV***mix. |
| *Staphylococcus aureus* 209P | BHI# | 0.2 | 0.1 | 0.2 | 0.2 | 0.2 | 0.1 |
| (EM)' | BHI# | 0.4 | 0.4 | 0.4 | 0.4 | 0.4 | 0.2 |
| (STH)' | BHI# | 0.8 | 0.8 | 1.6 | 1.6 | 1.6 | 0.8 |
| (PC,TC,EM,LM)'1 | BHI# | 6.25 | 6.25 | 6.25 | 6.25 | 6.25 | 0.2 |
| (PC,TC,EM,LM)'2 | BHI# | 6.25 | 6.25 | 6.25 | 6.25 | 6.25 | 0.2 |
| (TC,EM,LM,CP)' | BHI# | 6.25 | 6.25 | 6.25 | 6.25 | 6.25 | 0.2 |
| (SM,STH)' | BHI# | 0.4 | 0.2 | 0.2 | 0.4 | 0.4 | 0.2 |
| (PC,KM,NM)' | BHI# | 0.8 | 0.4 | 0.4 | 0.8 | 0.8 | 0.4 |
| (EM,CM,SM,PC,TC)' | BHI# | 0.4 | 0.2 | 0.4 | 0.4 | 0.4 | 0.2 |
| (EM,OM)' | BHI# | 0.8 | 0.4 | 0.8 | 0.8 | 0.8 | 0.4 |
| (TC,CP,PC)' | BHI# | 0.2 | 0.2 | 0.4 | 0.4 | 0.4 | 0.2 |
| (BX-1633)(PC)' | BHI# | 0.4 | 0.2 | 0.4 | 0.4 | 0.4 | 0.2 |
| Russell(PC)' | BHI# | 0.2 | 0.2 | 0.4 | 0.4 | 0.4 | 0.2 |
| Smith | BHI# | 0.2 | 0.2 | 0.2 | 0.4 | 0.4 | 0.2 |
| *Staphylococcus* sp. (PC)' | BHI# | 0.8 | 0.4 | 0.8 | 0.4 | 0.8 | 0.4 |
| sp. | BHI# | 0.8 | 0.8 | 0.8 | 0.8 | 0.8 | 0.4 |
| *Diplococcus pneumoniae* type 1 | BHI + HB§ | 0.2 | 0.4 | 0.2 | 0.4 | 0.4 | 0.1 |
| *Streptococcus pyogenes* | BHI + HB§ | 0.4 | 0.2 | 0.4 | 0.4 | 0.4 | 0.1 |
| *Sarcina lutea* | BHI# | 0.2 | 0.4 | 0.4 | 0.2 | 0.4 | 0.1 |
| *Bacillus subtilis* ATCC 6633 | BHI# | 0.4 | 0.4 | 0.8 | 0.8 | 0.8 | 0.4 |
| *Salmonella gallinarum* | BHI# | >25 | >25 | >25 | >25 | >25 | >25 |
| *Escherichia coli* | BHI# | >25 | >25 | >25 | >25 | >25 | >25 |
| *Pseudomonas aeruginosa* | BHI# | >25 | >25 | >25 | >25 | >25 | >25 |
| *Proteus vulgaris* | BHI# | >25 | >25 | >25 | >25 | >25 | >25 |
| *Candida albicans* | MY& | >25 | >25 | >25 | >25 | >25 | >25 |

*NV = neoviridogrisein; VG = viridogrisein; *GV = griseoviridin
(a) EM = erythromycin; STH = streptothricin; PC = penicillin; TC = tetracycline; LM = leucomycin; CP = chloramphenicol; SM = streptomycin; KM = kanamycin; NM = neomycin; OM = oleandomycin
( )' = resistant to the drug(s) in parenthesis
BHI = brain heart infusion broth;
§BHI + HB = brain heart infusion broth containing 10% horse blood;
&MY = malt extract-yeast extract medium As shown in the table of MIC values listed above, neoviridogrisein II is more active than neoviridogrisein IV, that is, viridogrisein. This MIC experiment was based on the two-fold dilutions. To differentiate neoviridogrisein II and viridogrisein in their antibiotic activity, the MIC determination was repeated with a far lower dilution rate. The subsequent table indicates that neoviridogrisein II is 2-3 times more active than viridogrisein.

TABLE 2

| Comparison of neoviridogrisein II with viridogrisein | | |
|---|---|---|
| | MIC (mcg/ml) | |
| Microorganism | NV*II | VG** |
| *Staphylococcus aureus* 209 P | 0.078 | 0.133 |
| (EM,CM,SM,PC,TC)' | 0.125 | 0.334 |
| (TC,CP,PC)' | 0.094 | 0.334 |
| Bx-1633(PC)' | 0.125 | 0.267 |

TABLE 3

| Synergism of neoviridogriseins mixture with griseoviridin | | |
|---|---|---|
| Neoviridogriseins mixture | Griseoviridin | MIC* (mcg/ml) |
| 100 | 0 | 0.313 |
| 90 | 10 | 0.156 |
| 80 | 20 | 0.125 |
| 70 | 30 | 0.125 |
| 60 | 40 | 0.094 |
| 50 | 50 | 0.078 |
| 40 | 60 | 0.094 |
| 30 | 70 | 0.125 |
| 20 | 80 | 0.250 |
| 10 | 90 | 0.250 |
| 0 | 100 | 0.250 |

*Test microorganism: *Sarcina lutea*

Tube dilution method with brain heart infusion broth.

The above table indicates that the synergistic action of the neoviridogriseins mixture with griseoviridin was most significant at the ratio of 50:50; that is, a 1:1 mixture of neoviridogriseins and griseoviridin is 3-4 times more active than neoviridogriseins or griseoviridin only.

The following table 4 reports the high in vitro activity of neoviridogrisein II against various Mycoplasma strains as well as the superior synergism shown by a mixture neoviridogrisein II-griseoviridin in comparison with a mixture viridogrisein-griseoviridin. The MIC were determined by the dilution method.

TABLE 4

| Microorganism | Medium | NV II | VG | GV | NV II + GV* | VG + GV* |
|---|---|---|---|---|---|---|
| *Mycoplasma gallisepticum* KP13 | (1) | 0.025 | 0.10 | 0.10 | 0.0063 | 0.025 |
| *Mycoplasma pulmonis* PG 22 | (2) | 0.78 | 1.56 | 6.25 | 0.20 | 0.39 |
| *Mycoplasma fermentans* | (2) | <0.05 | <0.05 | <0.05 | <0.05 | <0.05 |
| *Mycoplasma agalactiae* PG 2 | (2) | 0.39 | 0.78 | 3.13 | <0.05 | 0.39 |

Medium (1): PPLO enrichment broth (Eiken, Japan)
(2): PPLO broth (Chanock's medium; Difco)
*Mixing ratio: 50/50
NV II, VG, GV: see table 1

As illustrated above, the novel neoviridogriseins I-III of the present invention display a remarkable activity against gram-positive bacteria and mycoplasma strains both alone or in various admixtures with viridogrisein (neoviridogrisein IV) and griseoviridin. It has been found that the mutual weight proportions of neoviridogriseins I-III, viridogrisein (neoviridogrisein IV) and griseoviridin in a mixture may vary within very wide limits, but the surprising antimicrobial and antimycoplasma activities are still retained. As a representative, though not limitative example, a mixture having the following percent composition (by weight):
Neoviridogrisein II: 27%
Neoviridogrisein IV(viridogrisein): 23%
Griseoviridin: 50%
was tested in vitro against *Streptococcus mutans*, a microoganism associated with dental caries and peridontal diseases. The test was carried out in Todd Hewitt Broth (Difco) with 0.5% TC Lactalbumin hydrolysate (Difco). Initial organism count approximately $3 \times 10^4$ organisms per ml. Culture tubes were incubated anaerobically at 37° C. for 48 hours. The minimum inhibitory concentration (MIC) and minimum bactericidal concentration were both found at a neoviridogrisein concentration of 1.0 part per million (ppm).

In another representative, though not limitative example, the same mixture was tested in vitro against *Treponema hyodysenteriae*, a swine dysentery organism. The mixture was tested as dilutions in blood agar at concentrations of 100, 50, 10, 5, 1, 0.5 and 0.1 ppm. Plates were inoculated with a swab and incubated 4 days at 42° C. The MIC was determined to be 0.5 ppm.

In a further representative, though not limitative example, a mixture having the following percent composition (by weight):
Neoviridogrisein II: 25%
Neoviridogrisein IV (viridogrisein): 25%
Griseoviridin: 50%
was tested in vitro against several Mycoplasma strains.

The minimum inhibitory concentrations (MIC) were found to be as follows:
Strain: MIC
*Mycoplasma gallisepticum* KP13: 0.07
*Mycoplasma pulmonis*: 0.20
*Mycoplasma fermentans*: 0.05
*Mycoplasma agalactiae*: 0.05

These types of neoviridogriseins-griseoviridin mixtures are also useful in the treatment of animals suffering from infections diseases caused by the above pathogenic bacteria.

As mikamycins A and B have been known to be very effective as feed additive, the new antibiotic compounds of this invention were subjected to the animal feed test. Neoviridogriseins as mixture were added to the chicken feed at a rate of 2-20 ppm and fed to male chickens for 10 weeks. Compared with the control group of chicken which received the same feed without neoviridogriseins, the neoviridogrisein-fed chickens were superior in the increase rate of body weight and the feed efficiency. Thus neoviridogriseins of this invention have been proved very useful as feed additive.

Also the compositions containing one or more of the neoviridogriseins I-III, optionally in admixture with viridogrisein (neoviridogrisein IV) and griseoviridin, wherein the mutual weight proportions of the components may vary within very wide limits, proved to be very useful as feed additive.

As a representative, though not limitative example, a mixture having the following percent composition (by weight):
Neoviridogrisein II: 27%
Neoviridogrisein IV (viridogrisein): 23%
Griseoviridin: 50%
was tested in vivo by incorporation in the diet of growing chicks. One-day old cockerels, 15 birds per treatment were used. The chicks were maintained for 11 days on a feed containing about 55% rye grain, supplemented with vitamins, minerals, fat and protein sources. The high content of rye grain normally gives poor to moderate growth, and this diet is a standard one used for screening growth promoters and antibiotic feed additives. Penicillin (100 ppm) was used as a positive control. The data is tabulated below. Feed/Gain ratio is grams feed consumed per gram of weight gained. Body weight ratio is the ratio of chick body weight at the end of the 11 day study to the initial body weight. The last column is the average gain per bird (in grams).

| TREATMENT | DIET CONC PPM | FEED/ GAIN RATIO | BODY WEIGHT RATIO | (GMS) AVG B.W. GAIN |
|---|---|---|---|---|
| Rye Control | — | 1.334 | 4.696 | 156.47 |
| Penicillin | 100 | 1.197 | 5.012 | 163.20 |
| Tested mixture | 100 | 1.256 | 4.789 | 161.66 |
| Tested mixture | 50 | 1.283 | 4.892 | 163.47 |
| Tested mixture | 25 | 1.204 | 5.226 | 174.67 |

In the following, this invention will be further illustrated by preferred examples, but should not be construed as limited by those examples.

EXAMPLE 1

Seed culture medium consisting of soybean meal 0.5%, Pharmamedia (Traders Oil Mill Co.) 0.5%, oatmeal 0.5%, dry yeast 0.5% and beet molasses 0.5% was adjusted to pH 6.5 and distributed in a 50 ml. amount in a 250 Erlenmeyer flask. After autoclaving at 120° C. for 15 minutes, a loopful amount of Streptomyces sp. P 8648 on an ISP-2 agar slant was inoculated and the flask incubated at 28° C. for 48 hours on a rotary shaker. Two milliliters of the said seed culture was transferred into a 500 ml. Erlenmeyer flask containing 100 ml. of the following fermentation medium:

Soybean meal: 0.5%
Peanut meal: 0.5%
Oatmeal: 0.5% (pH 6.5 prior to autoclaving)
Dry yeast: 0.5%
Beet molasses: 0.5% and cultivated at 28° C. for 96 hours on a rotary shaker at 200 r.p.m. (radius of circle 3.5 cm.). The culture broth was collected from 12 flasks and filtered to give a clear broth filtrate. The obtained cake on the filter was washed with 100 ml. of water. The water washing and the broth filtrate were combined. The antibiotic activity of this solution (pH 8.3) was determined to be 23.0 mm on a nutrient agar assay plate of *Sarcina lutea* when the standardized disc assay was carried out with a 8 mm paper disc. Eight hundred milliliter of the said aqueous solution was twice extracted with 200 ml. each of n-butanol, and the butanol extracts were combined and evaporated to dryness under reduced pressure to yield 90 mg. of crude powder of neoviridogriseins and griseoviridin. This crude powder was mixed with a small amount of silica gel and applied on a silica gel column (Wako-Gel C-100, Wako Pure Chemical Industries, Ltd.; 1.5×25 cm.). The silica gel column was eluted first with 300 ml. of a benzene-acetone mixture (5:1), and then with a benzene-acetone mixture (2:1). Ten gram fractions were collected on an automatic fraction collector. Active fractions of Nos. 25 to 35 were combined and evaporated to dryness to provide 30 mg. of neoviridogrisein mixture (consisted of neoviridogriseins I, II and III and viridogrisein). In addition, evaporation of active fractions of Nos. 45-54 to dryness gave a crude powder, the antibiotic activity of which corresponded to griseoviridin by TLC. These two preparations were subjected to thin layer chromatography under the indicated conditions. The antimicrobial activity was detected on a nutrient agar assay plate of *Sarcina lutea*.

TLC plate: Pre-coated TLC plate SILICA GEL 60 F-254, E. Merck, Darmstadt.
(1) Solvent: Chloroform:methanol = 20:1
Neoviridogriseins Rf = 0.45
Griseoviridin 0.05
(2) Solvent: Benzene:acetone = 1:1
Neoviridogriseins Rf = 0.55
Griseoviridin 0.13

EXAMPLE 2

Two hundred milliliters of the 48 hour-old culture of Streptomyces sp. P8648 in the same culture medium as in Example 1 was inoculated into a 15 liter stainless steel jar fermenter containing 10 liters of the same seed culture medium as in Example 1 and cultivated at 27°-28° C. for 96 hours under forced aeration of 5 liters/min. of sterile air. The agitation during cultivation was performed at 200 r.p.m. with an impeller, the radius of which is about a fourth of the diameter of the jar fermenter. At the end of fermentation, the mycelia and solids were removed by filtration. The obtained broth filtrate was adjusted to pH 6.0 and extracted four times with 2 liters each of ethyl acetate. The ethyl acetate extracts were combined, dried over anhydrous sodium sulfate and evaporated to dryness under reduced pressure to yield 700 mg. of crude neoviridogriseins and griseoviridin. The recovered crude powder of neoviridogriseins and griseoviridin was dissolved in a small amount of methanol and charged on a Sephadex LH-20 column (3×50 cm.). Ten milliliter fractions were collected with methanol as an eluting solvent. Neoviridogriseins were located in fraction Nos. 22-29. These fractions were collected, concentrated to dryness and further purified by silica gel column chromatography (SILICAR CC-7 Special; Mallinckrodt Chemical Works; 1.5×20 cm.). The elution was run with a mixture of chloroform and methanol (30:1). Eight 5 gram fractions from fraction No. 5 to fraction No. 12 were combined and evaporated to dryness under reduced pressure to yield 25 mg. of white powder of neoviridogriseins. The percent composition of neoviridogriseins I, II and III and viridogrisein in this powder was as follows:

| Neoviridogrisein | I | 15% |
|---|---|---|
| | II | 20% |
| | III | 20% |
| Viridogrisein | | 45% |

Griseoviridin was found by TLC in fraction Nos. 30-34 of the said Sephadex LH-20. These active fractions were combined, evaporated to dryness under reduced pressure and crystallized in warm methanol to give 30 mg. of needle crystals of griseoviridin. The identity of these crystals with griseoviridin was proved by TLC and other physico-chemical determinations.

EXAMPLE 3

The same fermentation as described in Example 1 was carried out for 96 hours except that the fermentation medium was composed of soybean meal 0.5%, Pharmamedia 0.5%, oatmeal 0.5%, dry yeast 0.5%, beet molasses 0.5% and DL-alpha-amino-n-butyric acid 0.1% (pH 6.5). The fermentation broth was collected from 13 flasks and filtered. The filtered liquid was extracted with n-butanol (300 ml. each, twice). The removal of n-butanol from the extracts left about 70 mg. of crude powder of neoviridogriseins and griseoviridin. This crude powder was analysed by silica gel thin layer chromatography followed by bio-autography on *Sarcina lutea* as the test organism. The TLC plate employed in this assay was a product of E. Merck, Darmstadt (Pre-coated TLC plate SILICA GEL 60 F-254). The obtained Rf values and the solvent systems were as follows:

| Chloroform:methanol | | 20:1 | 30:1 | 40:1 |
|---|---|---|---|---|
| Neoviridogrisein | I | Rf = 0.60 | 0.39 | 0.20 |
| | II | 0.56 | 0.32 | 0.16 |
| | III | 0.50 | 0.19 | 0.13 |

| Chloroform:methanol | 20:1 | 30:1 | 40:1 |
|---|---|---|---|
| Viridogrisein | 0.43 | 0.18 | 0.10 |
| Griseoviridin | 0.05 | 0.02 | 0.00 |

EXAMPLE 4

Fifty milliliters of the seed culture medium containing 0.3% beef extract, 0.5% tryptone (Difco Laboratories), 0.1% glucose, 2.4% soluble starch, 0.5% yeast extract, 0.4% calcium carbonate and 0.5% soybean meal (pH 7.0) was distributed in a 250 ml. Erlenmeyer flask and autoclaved at 120° C. for 15 minutes. Spores of Streptomyces sp. P 8648 on a agar slant were seeded in the said flask and shake-cultured at 25° C. for 3 days to supply the seed culture. The fermentation medium was composed of 0.5% soluble starch, 2.0% glucose, 1.0% Pharmamedia, 0.5% oatmeal, 0.5% corn steep liquor, 0.05% dipotassium phosphate and 0.05% magnesium sulfate (pH 6.5). Fifty milliliters of this fermentation medium was placed in a 250 ml. conical flask and autoclaved at 120° C. for 15 minutes. The size of the inoculum was 2% (v/v). The fermentation flask was inoculated with the above described seed culture and incubated at 25° C. on a rotary shaker. Twenty four or 48 hours after inoculation, a sterilized solution of casamino acid (Difco Laboratories) or proline (pH 7.0) was added to a final concentration of 0.4% and the fermentation was continued. Four days after inoculation, the fermentation broth was filtered and the broth filtrate was extracted twice with an equal volume of ethyl acetate. The ethyl acetate extracts were combined and evaporated to dry powder under reduced pressure. This crude powder was taken in ethyl acetate and an aliquot amount of the solution was quantitatively spotted on a silica gel TLC plate. The TLC plate was developed in a solvent system of chloroform and methanol (100:1) and the solvent was evaporated off in the air. The same TLC plate was again developed in the said solvent system of chloroform and methanol (100:1). Each component of neoviridogriseins was located under ultra-violet light (3650 Å), scraped off from the TLC plate and suspended in a known volume of methanol. After the silica gel was removed by decantation, the amount of the antibiotics in the extracts was determined by the UV-assay method, knowing that the epsilon value at 305 nm is 8,000. The results of the UV-assay are as follows:

|  |  | None | Amino acid added Casamino acid | Proline |
|---|---|---|---|---|
| Neoviridogrisein | I | 2% | 2% | 2% |
|  | II | 9 | 40 | 60 |
|  | III | 4 | 3 | 3 |
| Viridogrisein |  | 85 | 55 | 35 |

EXAMPLE 5

About 10 liters of the 23 hour-old seed culture was prepared in a jar fermenter under the same condition as described in Example 2. The fermentation medium (600 liter) comprising 0.5% soybean meal, 0.5% Pharmamedia, 0.5% oatmeal, 0.5% dry yeast, 0.5% beet molasses and 0.1% DL-alpha-amino-n-butyric acid (pH adjusted to 6.5 prior to autoclaving) was steam-sterilized at 120° C. for 15 minutes in a 1400 liter stainless steel tank fermenter and cooled down to 28° C. To this tank fermenter, the above-mentioned seed culture (10 liters) was added and cultivated at 28° C. for 75 hours under forced aeration with stirring at 180 r.p.m. (by means of a double impeller; radius of circle, ¼ of the diameter of the tank fermenter), the sterile air being fed at 300 liters/minute through a sparger from the bottom of the tank. At the end of fermentation, the broth was filtered through a filter press. The broth filtrate was extracted twice with 150 liters each of n-butanol. The n-butanol extracts were combined, washed with a small volume of saturated NaCl solution, and concentrated to 2 liters in a rotary evaporator. At this stage, 20 grams of silica gel (WAKOGEL G-100, Wako Pure Chemical Industries, Ltd.) was added and the concentration in a rotary evaporator was further continued to complete dryness. The obtained antibiotics-silica gel mixture was suspended in a small amount of chloroform and put on top of a silica gel column (WAKOGEL C-100; 6.5×75 cm.). The elution of the antibiotic activities was carried out stepwise first with 7 liters of chloroform, then with 10 liters of a mixture of chloroform and methanol (50:1); and finally with methanol. Fraction Nos. 16-29 (300 g/fraction) which were found bio-active on Sarcina lutea (neoviridogriseins) were collected and concentrated to dryness under reduced pressure to yield a crude powder of neoviridogriseins. This crude powder was dissolved in a small volume of methanol and passed through a Sephadex LH-20 column (7.0×45 cm.), each fraction (100 g.) being eluted with methanol. About 15 grams of crude powder of neoviridogrisein mixture was recovered from fraction Nos. 6-15 after the solvent was removed by evaporation. Fraction Nos. 50-60 of the above described silica gel column contained griseoviridin. A similar purification procedure with Sephadex LH-20 (column size 7.0×45 cm.) as used for the neoviridogrisein mixture was repeated to provide 4 grams of crude griseoviridin.

EXAMPLE 6

For final purification, preparative thin layer chromatography with a silica gel TLC plate was employed. One gram of the crude neoviridogrisein mixture prepared in Example 5 was dissolved in 2 ml. of ethyl acetate and applied in bandwise fashion on ten silica gel TLC plates (Pre-coated TLC plate SILICA GEL 60 F-254). These TLC plates were first developed with a solvent system of chloroform and methanol (50:1). After the solvent was evaporated off in the air, the said TLC plates were subjected to a second development with a solvent system of chloroform and methanol (25:1). Neoviridogriseins I, II and III and viridogrisein were marked on the TLC plates under ultra-violet light (3650 A; BLAK-RAY UVL-22, Ultra-Violet Products, Inc.) and scraped off the elution. Each neoviridogrisein component was eluted with a small amount of methanol and evaporated to dryness. The recovered amount of each neoviridogrisein component in pure state was as follows:

| Neoviridogrisein | I | 16.7 mg. (less pure, oily) |
|---|---|---|
|  | II | 11.1 mg. (white powder) |
|  | III | 15.2 mg. (white powder) |
| Viridogrisein |  | 30.3 mg. (white powder) |

About 5 mg. each of the neoviridogriseins was hydrolyzed in 6N HCl at 110° C. for 36 hours in a sealed tube and subjected to thin layer chromatography, paper chromatography, high voltage paper electrophoresis and autoamino acid analysis. The presence of the following constituent compounds was found in each component:

| Neoviridogrisein I | 3-hydroxy-picolinic acid |
| --- | --- |
|  | threonine |
|  | leucine |
|  | proline |
|  | sarcosine |
|  | β,N—dimethylleucine |
|  | α-amino-n-butyric acid |
|  | phenylsarcosine |
| Neoviridogrisein II | 3-hydroxypicolinic acid |
|  | threonine |
|  | leucine |
|  | proline |
|  | sarcosine |
|  | β,N—dimethylleucine |
|  | alanine |
|  | phenylsarcosine |
| Neoviridogrisein III | 3-hydroxy-picolinic acid |
|  | threonine |
|  | leucine |
|  | hydroxyproline |
|  | sarcosine |
|  | β,N—dimethylleucine |
|  | alpha-amino-n-butyric acid |
|  | phenylsarcosine |
| Viridogrisein | 3-hydroxypicolinic acid |
|  | threonine |
|  | leucine |
|  | hydroxyproline |
|  | sarcosine |
|  | β,N—dimethylleucine |
|  | alanine |
|  | phenylsarcosine |

In addition the identity of neoviridogrisein IV with viridogrisein was further confirmed by IR, UV, NMR and mass spectrometry, thin layer chromatrography, hydrolysate analysis and antimicrobial spectrometry. On the other hand, the griseoviridin preparation obtained in Example 5 was crystallized in warm methanol to yield needle crystals. Then a part of the needle crystals were compared and identified with an authentic preparation of griseoviridin by IR, UV, NMR and mass spectrometry, thin layer chromatography, elementary analysis and other physico-chemical properties.

DESCRIPTION OF THE DRAWINGS

FIG. 11: I.R. spectrum of neoviridogrisein III (NVG III)-KBr tablet

FIG. 12: I.R. spectrum of neoviridogrisein IV (NVG IV,VG)-KBr tablet.

Figure 1:
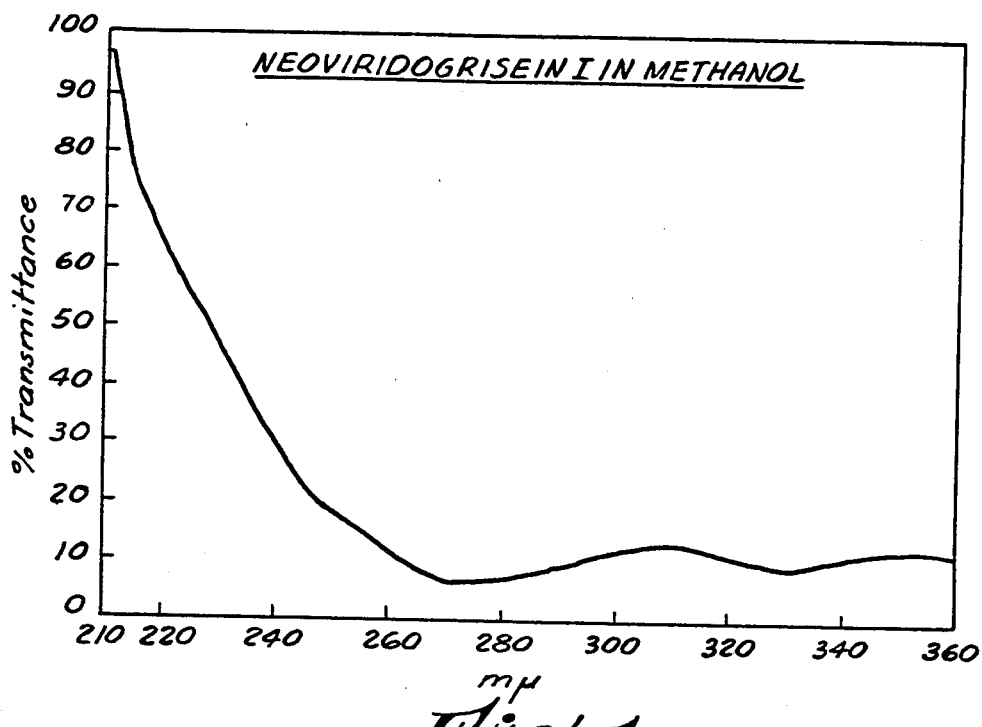
FIG. 1: UV spectrum of neoviridogrisein I (NVG I) in methanol
Figure 2:
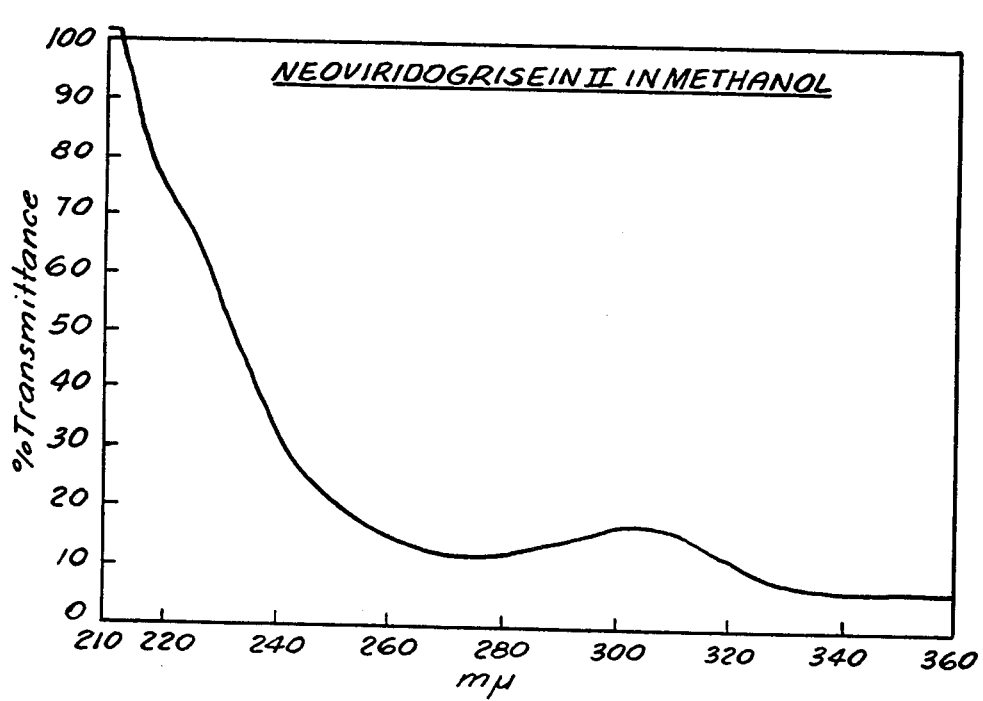
FIG. 2: UV spectrum of neoviridogrisein II (NVG II) in methanol
Figure 3:
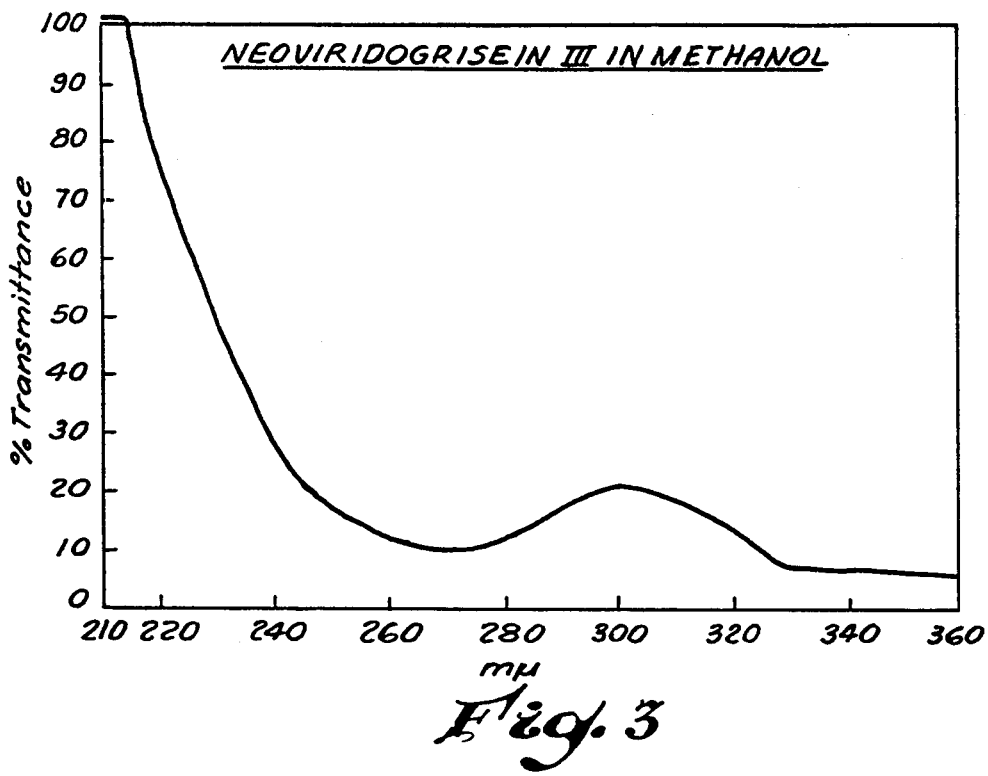
FIG. 3: UV spectrum of neoviridogrisein III (NVG III) in methanol
Figure 4:
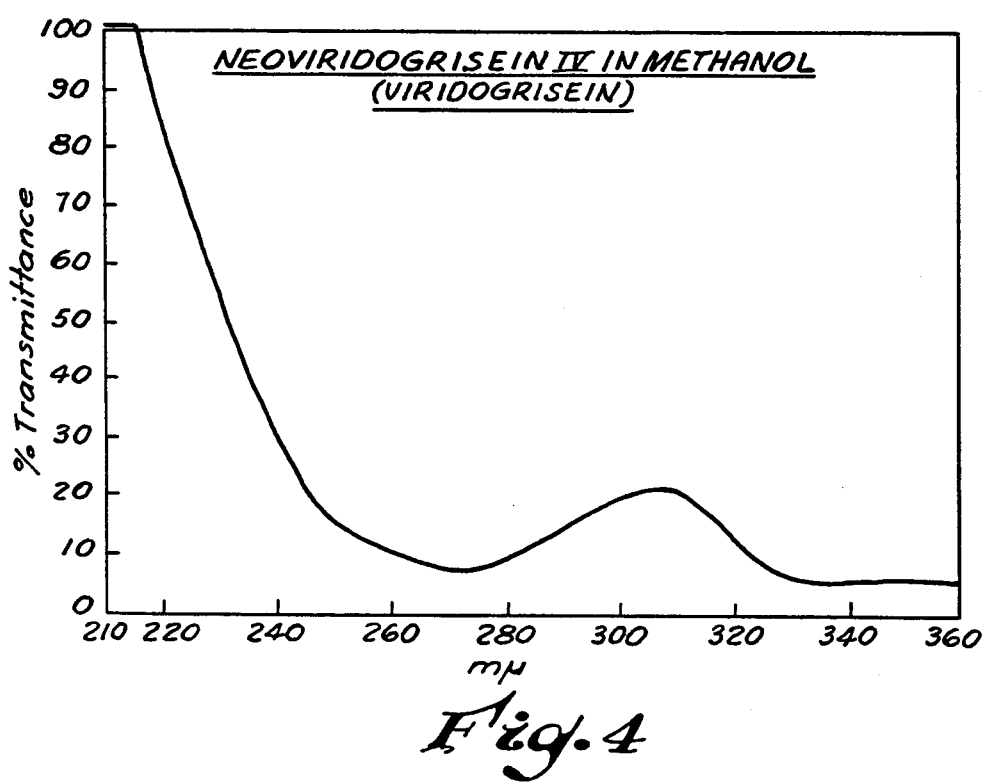
FIG. 4: UV spectrum of neoviridogrisein IV (NVG IV, VG) in methanol
Figure 5:
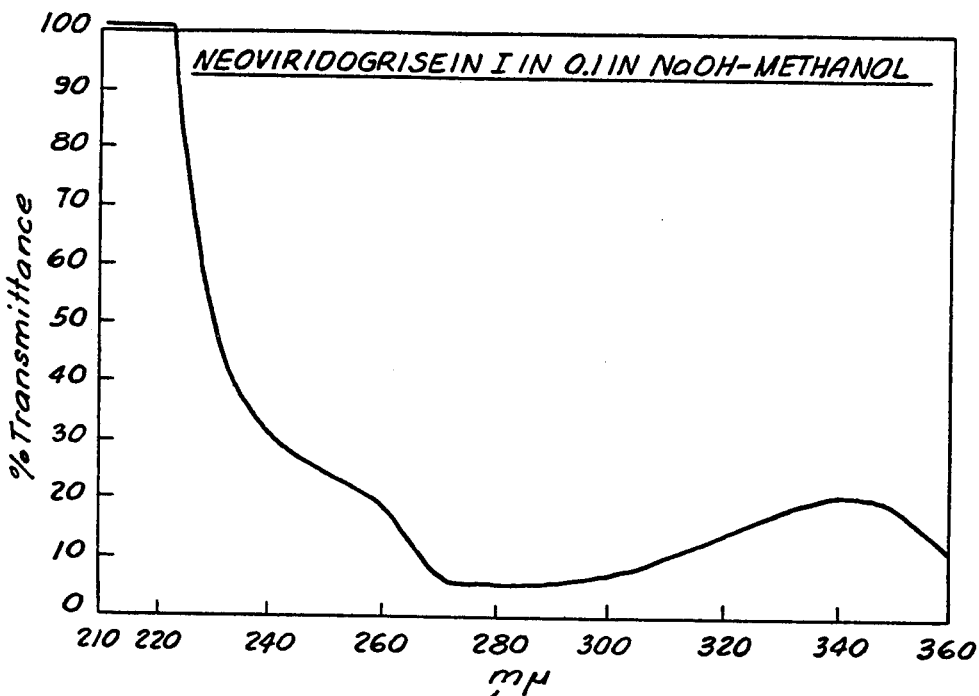
FIG. 5: UV spectrum of neoviridogrisein I (NVG I) in methanol/NaOH 0.1N
Figure 6:
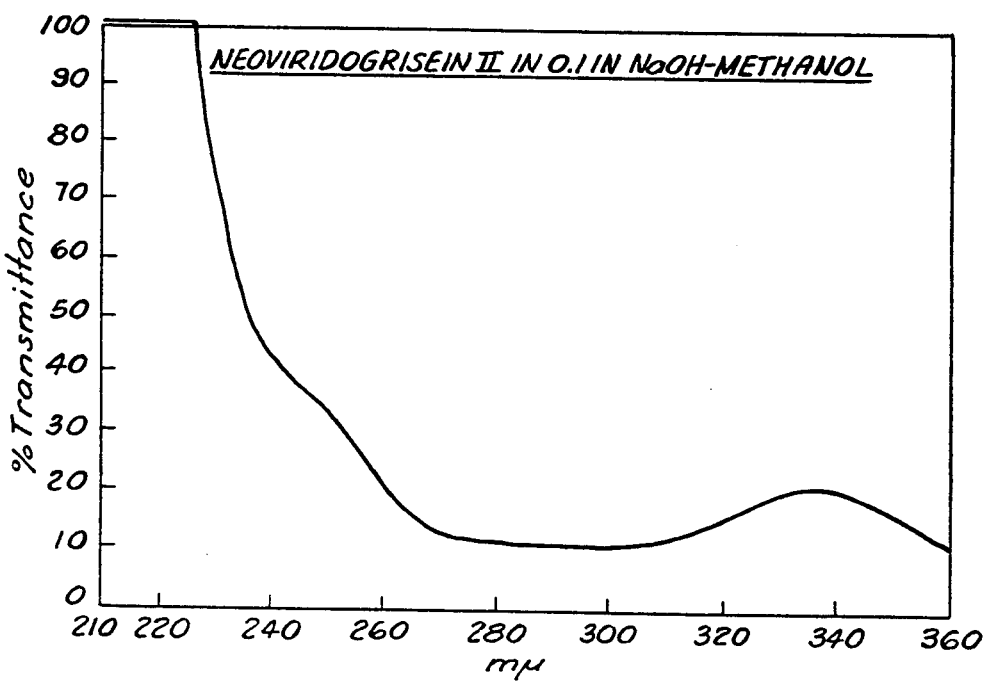
FIG. 6: UV spectrum of neoviridogrisein II(NVG II) in methanol/NaOH 0.1N
Figure 7:
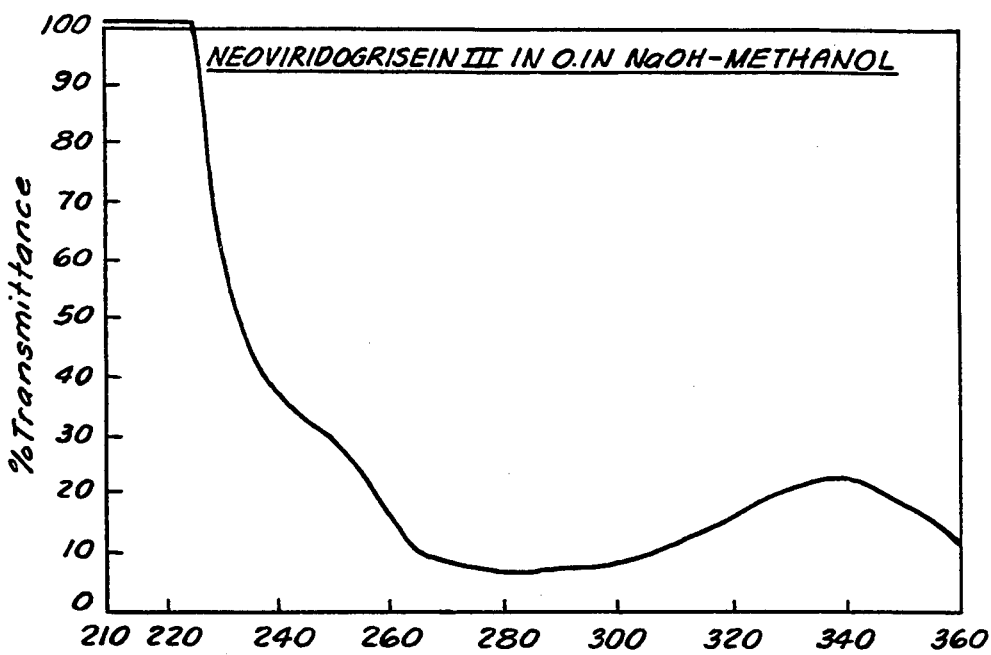
FIG. 7: UV spectrum of neoviridogrisein III(NVG III) in methanol/NaOH 0.1N
Figure 8:
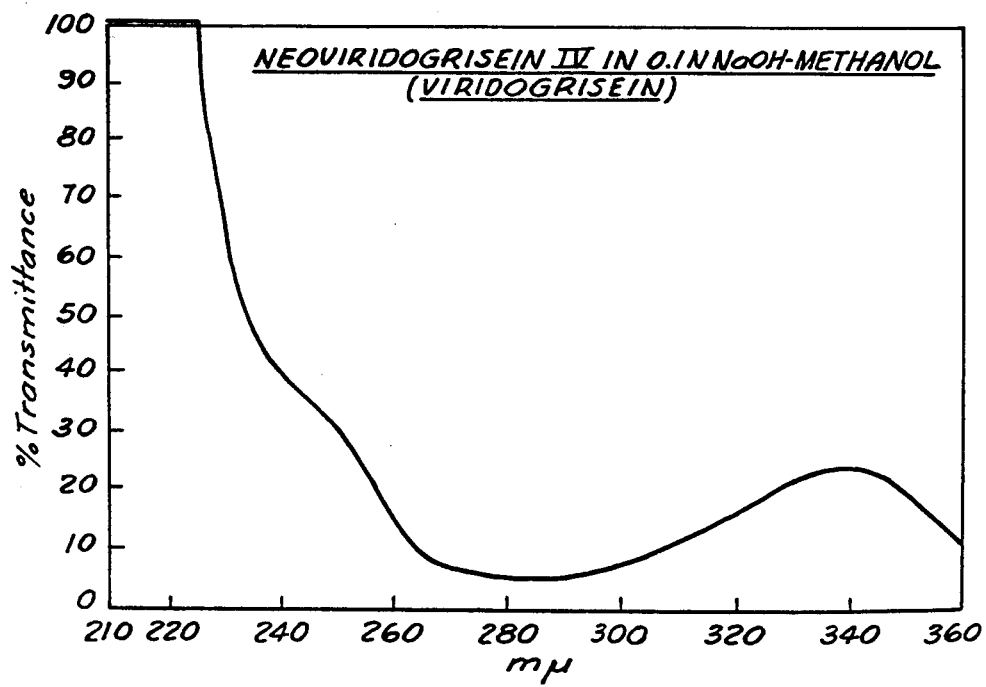
FIG. 8: UV spectrum of neoviridogrisein IV (NVG IV,VG) in methanol/NaOH 0.1N
Figure 9:
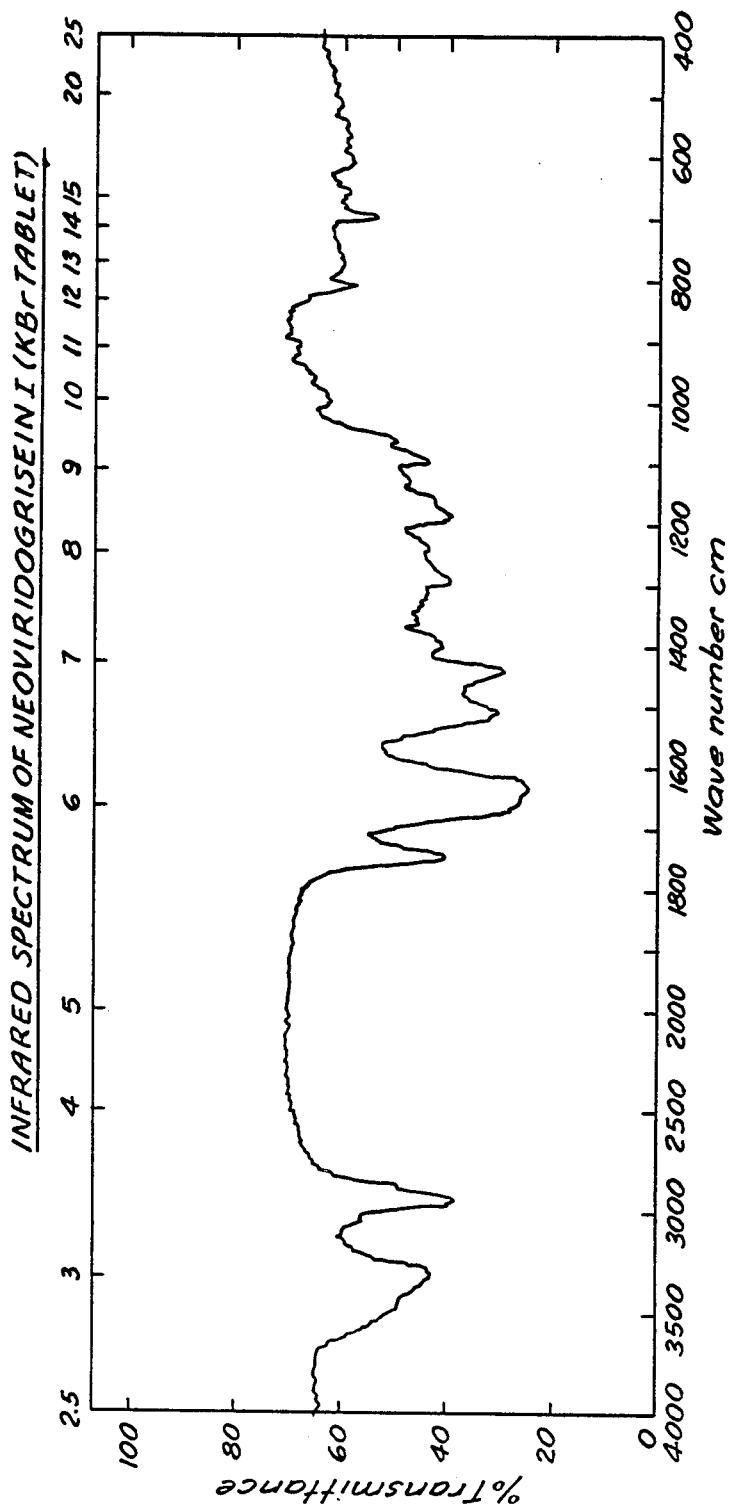
FIG. 9: I.R. spectrum of neoviridogrisein I (NVG I)-KBr tablet
Figure 10:
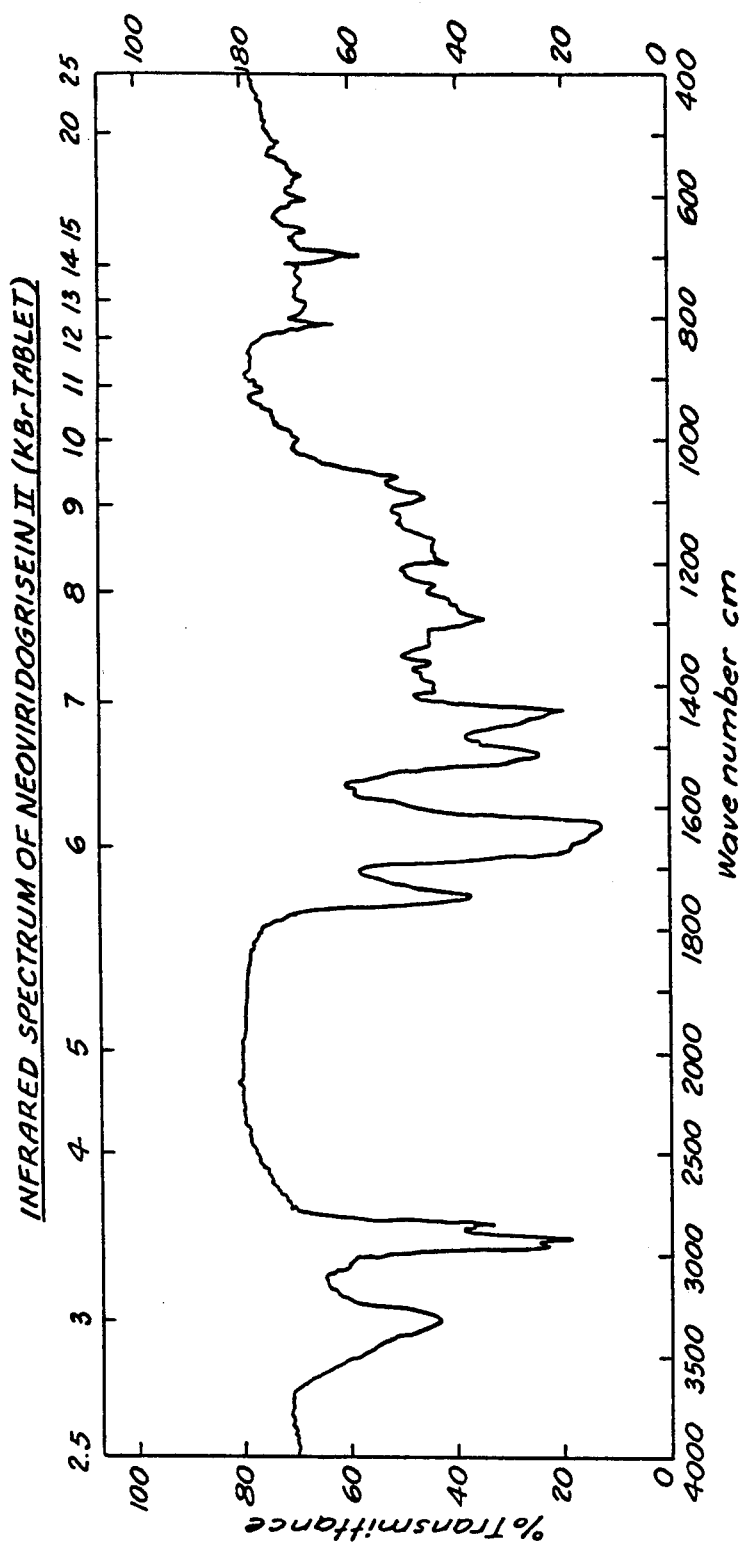
FIG. 10: I.R. spectrum of neoviridogrisein II (NVG II)-KBr tablet

We claim:
1. The antibiotic substance neoviridogrisein I of the formula

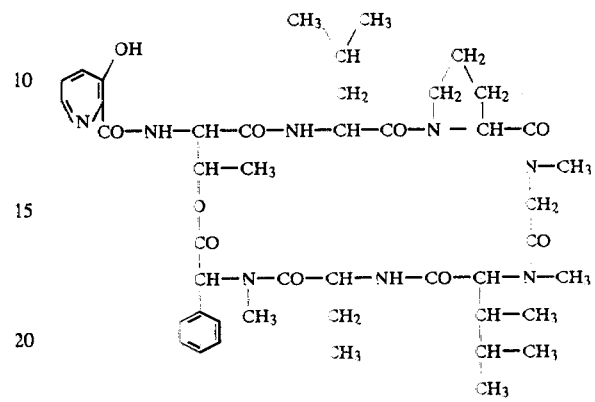

2. The antibiotic substance neoviridogrisein II of the formula

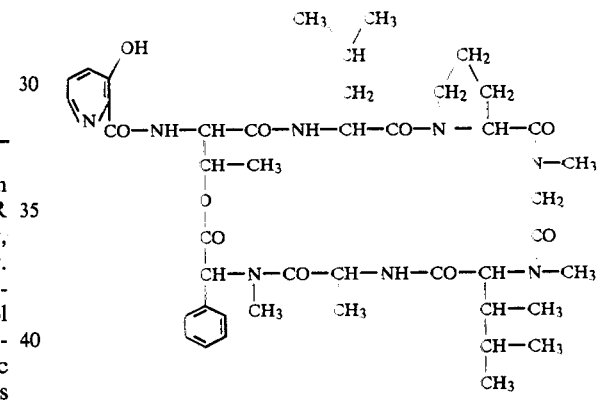

3. The antibiotic substance neoviridogrisein III of the formula

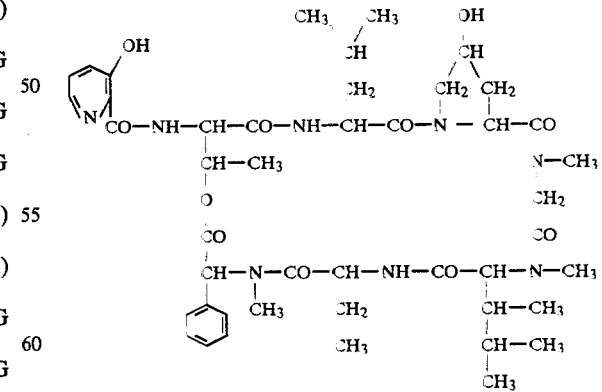

4. A composition which comprises an inert carrier and an antibiotically-effective amount of viridogrisein and one or more of the antibiotic materials selected from the group consisting of neoviridogrisein I, neoviridogrisein II, and neoviridogrisein III.

5. A composition comprising an inert carrier and an antibiotically-effective amount of an antibiotic material selected from the group consisting of neoviridogrisein I, neoviridogrisein II, neoviridogrisein III, and a mixture thereof.

6. The composition of claim 5 wherein the antibiotic material is neoviridogrisein I.

7. The composition of claim 5 wherein the antibiotic material is neoviridogrisein II.

8. The composition of claim 5 wherein the antibiotic material is neoviridogrisein III.

9. A composition comprising an inert carrier and an antibiotically-effective amount of neoviridogrisein I, neoviridogrisein II, neoviridogrisein III and viridogrisein in admixture with griseoviridin.

10. An animal feed composition comprising an animal feed in admixture with an antibiotically-effective amount of neoviridogrisein I, neoviridogrisein II, neoviridogrisein III, viridogrisein and griseoviridin.

11. An animal feed composition comprising an animal feed in admixture with an antibiotically-effective amount of an antibiotic material selected from the group consisting of neoviridogrisein I, neoviridogrisein II, neoviridogrisein III, and a mixture thereof.

12. The composition of claim 11 wherein the antibiotic material is neoviridogrisein II.

13. An animal feed composition comprising an animal feed in admixture with an antibiotically-effective amount of an antibiotic material selected from the group consisting of neoviridogrisein I, neoviridogrisein II and neoviridogrisein III, and a mixture thereof, in admixture with viridogrisein and griseoviridin.

14. The composition of claim 13 wherein the antibiotic material is neoviridogrisein II.

* * * * *